(12) United States Patent
Li

(10) Patent No.: US 9,508,608 B2
(45) Date of Patent: Nov. 29, 2016

(54) MONITORING LASER PROCESSING OF SEMICONDUCTORS BY RAMAN SPECTROSCOPY

(71) Applicant: Applied Materials, Inc., Santa Clara, CA (US)

(72) Inventor: Jiping Li, Palo Alto, CA (US)

(73) Assignee: APPLIED MATERIALS, INC., Santa Clara, CA (US)

( * ) Notice: Subject to any disclaimer, the term of this patent is extended or adjusted under 35 U.S.C. 154(b) by 29 days.

(21) Appl. No.: 14/305,435

(22) Filed: Jun. 16, 2014

(65) Prior Publication Data

US 2014/0370627 A1 Dec. 18, 2014

Related U.S. Application Data

(60) Provisional application No. 61/835,968, filed on Jun. 17, 2013.

(51) Int. Cl.
*G01R 31/26* (2014.01)
*H01L 21/66* (2006.01)
*G01N 21/65* (2006.01)
*H01L 21/67* (2006.01)

(52) U.S. Cl.
CPC .............. *H01L 22/12* (2013.01); *G01N 21/65* (2013.01); *H01L 21/67115* (2013.01); *H01L 21/67253* (2013.01); *H01L 22/26* (2013.01); *G01N 2201/0697* (2013.01)

(58) Field of Classification Search
CPC . H01L 22/12; H01L 21/02675; H01L 22/26; H01L 21/67115; H01L 21/67253; H01L 21/66; H01L 21/02; G01N 21/255; G01N 21/65; G01N 2201/0697; G01N 21/02
See application file for complete search history.

(56) References Cited

U.S. PATENT DOCUMENTS

| | | | |
|---|---|---|---|
| 2005/0037615 A1* | 2/2005 | Cabib | G01J 3/44 438/689 |
| 2006/0281068 A1* | 12/2006 | Maier | G01N 21/65 435/4 |
| 2012/0312790 A1* | 12/2012 | Moffatt | B23K 26/0626 219/121.6 |

* cited by examiner

*Primary Examiner* — Alexander Ghyka
*Assistant Examiner* — Abdulfattah Mustapha
(74) *Attorney, Agent, or Firm* — Patterson & Sheridan, LLP

(57) ABSTRACT

A Raman probe is used to detect crystal structure of a substrate undergoing thermal processing in a thermal processing system. The Raman probe may be coupled to a targeting system of a laser thermal processing system. The Raman probe includes a laser positioned to direct probe radiation through the targeting system to the substrate, a receiver attuned to Raman radiation emitted by the substrate, and a filter that blocks laser radiation reflected by the substrate. The Raman probe may include more than one laser, more than one receiver, and more than one filter. The Raman probe may provide more than one wavelength of incident radiation to probe the substrate at different depths.

15 Claims, 2 Drawing Sheets

MONITORING LASER PROCESSING OF SEMICONDUCTORS BY RAMAN SPECTROSCOPY

CROSS-REFERENCE TO RELATED APPLICATIONS

This application claims benefit of U.S. Provisional Patent Application Ser. No. 61/835,968, filed Jun. 17, 2013, which is incorporated herein by reference.

FIELD

Embodiments described herein relate to apparatus and methods of thermal processing. More specifically, apparatus and methods described herein relate to methods and apparatus for laser processing of semiconductor substrates.

DESCRIPTION OF THE RELATED ART

Thermal processing is commonly practiced in the semiconductor industry. Semiconductor substrates are subjected to thermal processing in the context of many transformations, including doping, activation, and annealing of gate source, drain, and channel structures, siliciding, crystallization, oxidation, and the like. Over the years, techniques of thermal processing have progressed from simple furnace baking, to various forms of increasingly rapid thermal processing such as RTP, spike annealing, and laser annealing.

In some processes, it is desired to melt a portion of the semiconductor substrate. As device geometries shrink, the degree or depth of melting needed also shrinks. Monitoring the depth of melting becomes increasingly important for uniform processing.

Laser annealing processes are increasingly used for thermal processing in the semiconductor industry. Lasers are able to deliver robust amounts of energy in very short times allowing thermal treatment of a thin layer or a shallow depth of a layer. The short time scales, coupled with the very shallow melt depths desired for many applications, lead to very demanding process windows for laser melt annealing applications. Thus, there is a need for apparatus and methods of monitoring melt depth of a semiconductor substrate over very short time frames and very shallow melt depths during thermal processing.

SUMMARY OF THE INVENTION

A system is disclosed for thermal processing of substrates. A substrate support is disposed facing a source of intense radiation such that the intense radiation may be directed to a target location for treatment of a substrate on the substrate support. A targeting system is disposed along an optical path of the intense radiation and facilitates identifying the target location for treatment.

A Raman probe is coupled to the targeting system. The Raman probe includes a laser positioned to direct probe radiation through the targeting system to the substrate, a receiver attuned to Raman radiation emitted by the substrate, and a filter that blocks laser radiation reflected by the substrate. The Raman probe may include more than one laser, more than one receiver, and more than one filter. The Raman probe may provide more than one wavelength of incident radiation to probe the substrate at different depths. Radiation received by the Raman probe may be analyzed to determine crystal properties of the substrate at the target location.

BRIEF DESCRIPTION OF THE DRAWINGS

So that the manner in which the above-recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Figure 1:
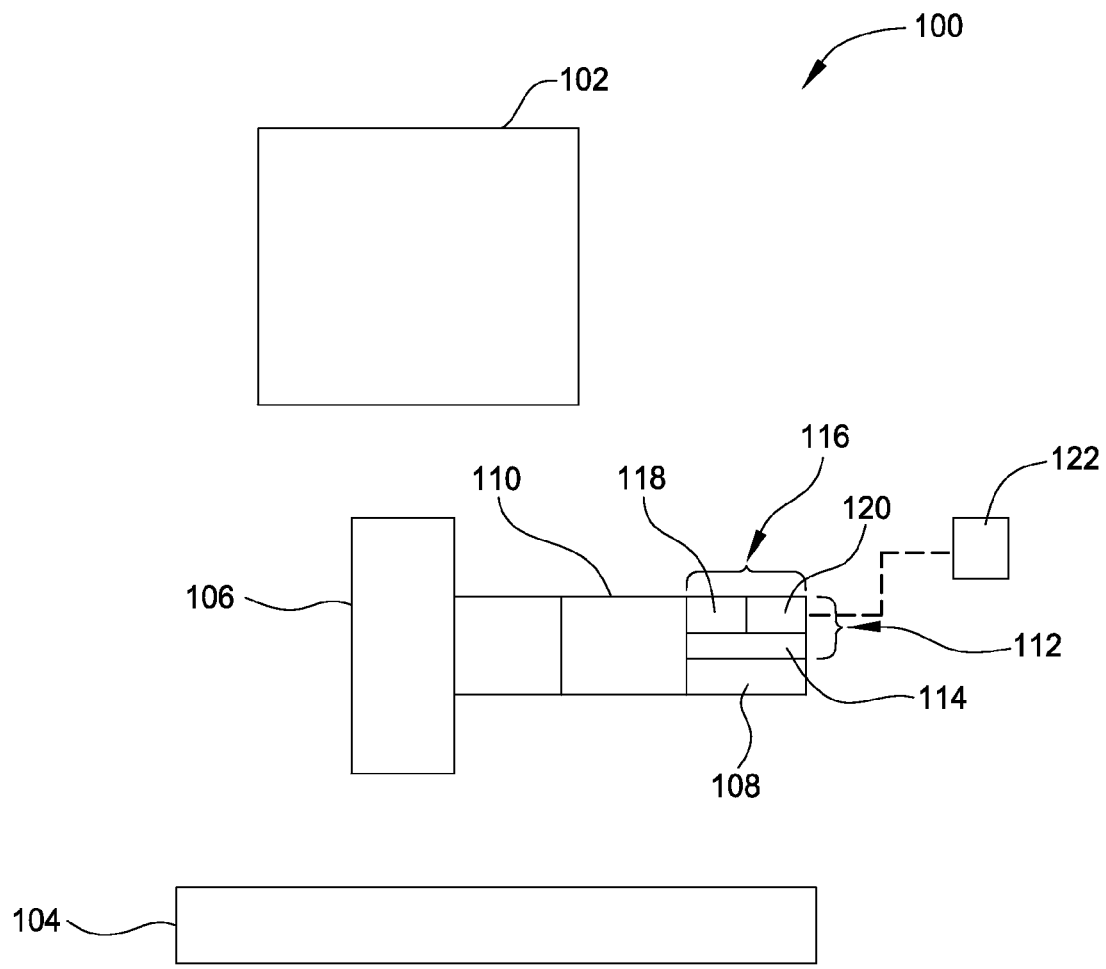
FIG. 1 is a schematic diagram of a thermal processing apparatus according to one embodiment.

Apparatus and methods for thermal treatment of substrates and monitoring such thermal treatment are provided. FIG. 1 is a schematic view of a thermal treatment apparatus 100 according to one embodiment. The thermal treatment apparatus includes an intense radiation source 102, such as a laser, that produces intense radiant energy that may be annealing energy. The intense radiation source 102 may be a pulsed radiation source having a pulse length from about 1 nsec to about 100 nsec. The pulses are directed toward a substrate disposed on a substrate support 104 and carry thermal energy into the substrate to perform a thermal treatment. Typically a portion of the substrate is treated by directing one or more pulses of radiation to the portion, after which the substrate or the intense radiation source 102 is moved to expose a subsequent portion of the substrate. Successive exposures are performed until all desired areas of the substrate are treated.

The apparatus 100 includes a targeting system 106 that produces a view of the substrate along an optical path of the intense pulsed light source 102. The targeting system 106 provides visibility of the alignment of the intense pulsed light source 102 with the desired portion of the substrate. The targeting system 106 typically includes a microscope 108 and optics 110 to deliver an image of the substrate to the microscope 108. An exemplary thermal processing apparatus that features a pulsed laser source of intense radiation is described in commonly owned United States Patent Application Publication 2012/0329178, which is incorporated herein by reference.

A Raman spectrometer 112 is coupled to the targeting system 106. The Raman spectrometer 112 includes a laser 114, which may be a pulsed laser or a CW laser, and a receiver 116. The receiver 116 contains a narrow band filter 118 that blocks light reflected by the substrate at the laser wavelength and a spectrometer 120 that records the light spectrum passed by the filter. The receiver is attuned to Raman radiation emitted by the substrate. Thus, the spectrometer receives Raman emissions from the substrate. The receiver 116 may be coupled to a recording device 122, such as a computer, to record a signal from the spectrometer 120 over time.

The spectrum recorded by the Raman spectrometer indicates composition and structure of the substrate. The light from the laser penetrates the surface of the substrate to a depth that depends on the light wavelength and intensity. The light recorded by the Raman spectrometer indicates an average composition and structure of the penetrated depth of the substrate. In particular, different crystal morphologies of semiconductor materials produce different Raman signals. Amorphous silicon, for example, registers a broad Raman peak around 450 cm$^{-1}$ while crystalline silicon registers a narrow peak at 520 cm$^{-1}$. Polycrystalline silicon registers between the amorphous and crystalline peaks, depending on the grain size.

The targeting system 106 may be used to locate a target spot for Raman analysis, and a sample Raman reading may be taken from the target spot. The spectrum recorded may then be integrated to give a numerical value that represents a degree of crystallinity of the target spot to a depth dependent on the wavelength of laser light. If desired, more than one wavelength may be sampled to record a sample from two different depths of the substrate surface. By comparing the two samples, an integrated crystallinity figure may be determined for a layer within the substrate.

The laser used for Raman spectroscopy may be any kind of laser that produces wavelengths that penetrate to a desired depth within a semiconductor substrate. Solid state lasers, such as Nd:YAG, Nd:glass, and the like may be used. Fiber lasers may also be used operating at wavelengths from 600 nm to 300 nm. If the laser is tunable, a plurality of wavelengths may be selected. For example, a tunable laser operating at wavelengths between about 532 nm and about 300 nm may be used to sample, for example 10 different depths of the substrate. Subtracting the signals appropriately provides a crystallinity measure for a number of layers equal to the number of different wavelengths sampled. The lasers used for Raman spectroscopy are typically low power, operating for example at power levels of a few watts down to milliwatts. The Raman laser may operate at a power level between about 1 mW and about 10 W.

Sampling a plurality of wavelengths using more than one wavelength of light may reveal a crystallinity profile in relation to depth within the substrate. Longer wavelength light generally penetrates deeper into a substrate than shorter wavelength light. More than one laser, each laser operating at a different wavelength, may be used to collect Raman readings representing different depths. Alternately, a tunable laser, a chirped laser, or a broadband laser may be used to provide multiple wavelengths for a Raman probe. The tunable laser may be operated to provide a first Raman reading at a first wavelength and a second Raman reading at a second wavelength. Each of the first Raman reading and the second Raman reading may be integrated to provide a measure of crystallinity at two different depths in the substrate. In this way, a crystallinity profile may be constructed based on depth within the substrate. If a chirped laser is used, the Raman radiation received from the substrate may be recorded as a function of time by storing the detector output in an electronic storage device, such as a computer. The time variation of the received signal may be related to wavelength of the incident laser light over the duration of the chirped laser pulse to relate the signal to depth within the substrate. A similar process may be followed when using a broadband laser to provide the incident radiation. Longer wavelength photons from the laser will penetrate deeper into the substrate, and will thus travel a longer optical path than the shorter wavelength photons to arrive at the detector later. Storing the received signal and relating the time variation of the signal to wavelength, and ultimately to depth within the substrate, allows a crystallinity profile with depth to be ascertained.

In one example, a first pulse of thermal processing energy may be delivered to a portion of the substrate to change the crystal structure of the substrate, either from a high crystallinity state to a low crystallinity state, or vice versa, increasing or decreasing grain size. The Raman probe may be operated in CW during delivery of the first pulse, and the spectrum of radiation after the first pulse may be compared to the spectrum before the first pulse to determine a change in the crystal structure of the treated portion of the substrate. The spectrum after the first pulse may also be compared to a desired or target spectrum to determine whether an end point has been reached. A second pulse of thermal processing energy may be delivered to the portion of the substrate, and the Raman spectrum may be obtained following the second pulse to determine progression of the thermal process. Pulses of thermal processing radiation may be delivered to the portion of the substrate until the measured spectrum matches a desired spectrum, or until the change to the measured spectrum falls below a tolerance level.

The Raman laser spot may be focused or defocused to a desired spot size for sampling the composition and/or structure of the substrate. The Raman spot may be the same shape as the thermal processing radiation spot. For example, both the thermal processing radiation spot and the Raman spot may be square, circular, oval, or any desired shape, which may be achieved using shaped apertures or other optical elements. The Raman spot may be substantially the same size as the thermal processing radiation spot, or the Raman spot may be smaller than the thermal processing radiation spot.

More than one Raman probe may be used to probe the crystal structure at the thermal processing spot, if desired. A first Raman probe may use a first probe radiation at a first operating frequency, and a second Raman probe may use a second probe radiation at a second operating frequency different from the first operating frequency. The first operating frequency and the second operating frequency will penetrate the substrate surface to different depths, energizing Raman emissions from the substrate at different depths. The different Raman emissions will reveal the crystal structure of the substrate at the different depths. Thus, the first Raman probe may reveal crystal morphology at a first depth and the second Raman probe may reveal crystal morphology at a second depth. The two morphology readings may be used to determine the effect of the thermal processing radiation at the different depths.

Figure 2:
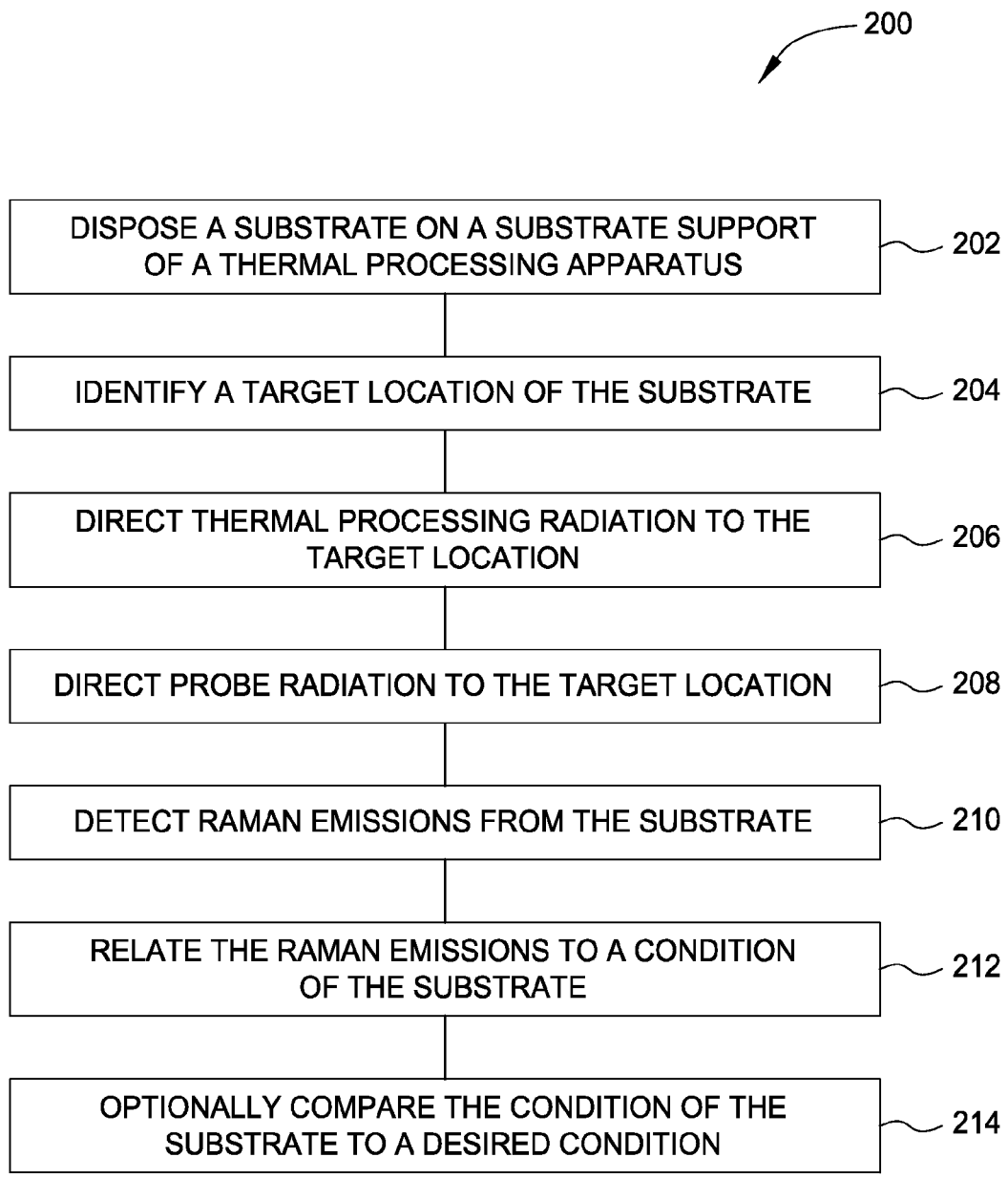
FIG. 2 is a flow diagram summarizing a method according to another embodiment.

FIG. 2 is a flow diagram summarizing a method 200 according to another embodiment. The method 200 may be used to thermally process a substrate such as a semiconductor substrate, for example a silicon substrate. At 202, the substrate is disposed on a substrate support in a thermal processing apparatus. The thermal processing apparatus may be a laser processing apparatus, as described above, which may be pulsed.

At 204, a target location of the substrate is identified. The target location is typically a area of the substrate surface that has an extent less than the areal extent of the substrate. Thus, the target location is typically a portion of the substrate surface. The targeting system described above in connection with FIG. 1 may be used to identify the target location.

Alternately, the target location may be identified by a predetermined offset from a previously identified location.

At 206, thermal processing radiation is directed to the target location of the substrate. The thermal processing radiation may be annealing radiation, crystallizing radiation, or pre-heating radiation. The thermal radiation may be laser radiation, which may be pulsed. Laser radiation for thermal processing may be any suitable wavelength from about 200 nm to about 1,500 nm, for example about 532 nm. The thermal processing apparatus described above in connection with FIG. 1 may be used to perform the thermal process.

At 208, probe radiation is directed to the target location. The probe radiation is typically selected to yield an emission of Raman radiation from the substrate. The probe radiation may be delivered at one or more wavelengths. Delivering more than one wavelength of probe radiation may facilitate receiving Raman emissions from different depths within the substrate since incident radiation of different wavelengths will penetrate to different depths of the substrate.

At 210, Raman emissions from the substrate are recorded. A spectrometer may be used to record the Raman emissions. The spectrometer may include, or may be coupled to, a recording device that enables recording a signal based on the Raman emissions in a time series. Recording a time series signal of the Raman emissions allows analysis of the signal at different times representing emissions from different depths and target locations of the substrate.

At 212, the Raman emissions are related to a condition of the substrate, such as crystal state, at the target location or at the location from which the Raman emissions are received. The depth from which the Raman emissions emanate may be determined from the wavelength of the incident light. The crystal structure may be ascertained from the Raman emissions by comparing the recorded spectrum to a known spectrum to determine crystal structure, crystal morphology, and/or degree of crystallinity of the substrate at the target location. If more than one wavelength of probe radiation is used, the crystal structure may be ascertained at more than one depth within the substrate to determine a crystallinity profile with depth. The signal based on the Raman emissions may be integrated, or otherwise mathematically processed, to form a metric that represents the crystal state of the substrate at the target location. It should be noted that, in addition to ascertaining crystal state of the substrate, dopant activation may be determined by selecting the appropriate probe radiation and Raman emissions for analysis.

At 214, the condition of the substrate ascertained at 212 may optionally be compared to a desired condition to determine whether an action is to be taken. In this way, an endpoint may be determined to discontinue thermal processing when, for example, crystal state of the substrate reaches a desired condition. Alternately, a control signal may be generated to alter the thermal process according to the Raman signal. For example, based on the Raman signal, intensity of the thermal processing radiation may be increased or decreased, or an additional pulse of thermal processing radiation may be delivered to the target location. In this way, the condition of the target location may be ascertained after each pulse or increment of thermal processing radiation is delivered.

While the foregoing is directed to embodiments of the present invention, other and further embodiments of the invention may be devised without departing from the basic scope thereof, and the scope thereof is determined by the claims that follow.

The invention claimed is:

1. An apparatus for thermally treating a substrate, comprising:
    a source of directed thermal processing radiation;
    a substrate support disposed to receive the thermal processing radiation from the source at a target location;
    a targeting system disposed along a path of the thermal processing radiation; and
    a Raman probe coupled to the targeting system, the Raman probe comprising a laser positioned to direct probe radiation through the targeting system, a receiver attuned to one or more wavelengths of Raman radiation emitted by the substrate, and a filter that blocks laser radiation reflected from the substrate, wherein the Raman probe is located away from a path of the thermal processing radiation.

2. The apparatus of claim 1, further comprising a microscope to adjust the probe radiation to a desired area at the target location.

3. The apparatus of claim 2, wherein the Raman probe further comprises two or more radiation sensors that sample the probe radiation from different locations of the desired area.

4. An apparatus for thermally processing a substrate, comprising:
    a source of pulsed and directed thermal processing radiation;
    a substrate support disposed to expose a target to the thermal processing radiation;
    a Raman probe comprising a first laser and a second laser, the first and second lasers being disposed to direct a first probe radiation and a second probe radiation, respectively, to the target; and
    a targeting system that directs the thermal processing radiation, the first probe radiation, and the second probe radiation to the target, wherein the first laser has a first operating frequency and the second laser has a second operating frequency different from the first operating frequency.

5. The apparatus of claim 4, further comprising a sensor operable to differentiate Raman radiation of different crystal morphologies.

6. The apparatus of claim 1, further comprising a second Raman probe coupled to the targeting system.

7. The apparatus of claim 6, wherein each Raman probe comprises a laser positioned to direct probe radiation through the targeting system, a receiver attuned to one or more wavelengths of Raman radiation emitted by the substrate, and a filter that blocks laser radiation reflected from the substrate.

8. The apparatus of claim 6, wherein the Raman probe and the second Raman probe operate at different frequencies.

9. The apparatus of claim 7, further comprising a microscope to adjust the probe radiation to a desired area at the target location.

10. The apparatus of claim 3, further comprising a recording device coupled to the Raman probe.

11. The apparatus of claim 4, further comprising a recording device coupled to the Raman probe.

12. The apparatus of claim 4, wherein the Raman probe is located away from a path of the thermal processing radiation.

13. The apparatus of claim 4, wherein the targeting system comprises a microscope.

14. The apparatus of claim 13, further comprising a sensor operable to differentiate Raman radiation of different crystal morphologies.

15. An apparatus for thermally treating a substrate, comprising:
- a pulsed source of thermal processing radiation;
- a substrate support disposed to receive the thermal processing radiation from the source at a target location;
- a targeting system comprising a microscope disposed along a path of the thermal processing radiation; and
- a Raman probe coupled to the targeting system, the Raman probe including a laser to deliver probe radiation through the targeting system, a receiver to receive Raman radiation emitted by the substrate, and a narrow band filter to block laser radiation reflected by the substrate.

* * * * *